United States Patent [19]

Crosby

[11] Patent Number: 4,862,730

[45] Date of Patent: Sep. 5, 1989

[54] TEST METHOD FOR DETERMINATION OF MOISTURE VAPOR TRANSMISSION RATE

[75] Inventor: Philip M. Crosby, Northeast, Md.

[73] Assignee: W. L. Gore & Associates, Inc., Newark, Del.

[21] Appl. No.: 252,832

[22] Filed: Oct. 3, 1988

[51] Int. Cl.⁴ .............................................. G01N 5/02
[52] U.S. Cl. ................................................... 73/38
[58] Field of Search ................................. 73/38, 64.3

[56] References Cited

U.S. PATENT DOCUMENTS

| | | | |
|---|---|---|---|
| 2,012,762 | 8/1935 | Kern | 73/38 X |
| 2,400,481 | 5/1946 | Brabender | 73/38 X |
| 2,904,996 | 9/1959 | Lamb et al. | 73/38 |
| 3,286,509 | 11/1966 | Gluckman et al. | 73/38 |
| 4,532,316 | 7/1985 | Henn | 528/59 |
| 4,581,921 | 4/1986 | Gillespie et al. | 73/38 X |
| 4,741,202 | 5/1988 | Gillespie et al. | 73/38 X |

FOREIGN PATENT DOCUMENTS

| | | | |
|---|---|---|---|
| 3641821 | 6/1988 | Fed. Rep. of Germany | 73/38 |
| 1244096 | 7/1986 | U.S.S.R. | 73/38 |

OTHER PUBLICATIONS

Amdur, E. J., *Test Results from Fast WVT Unit.* In Modern Packaging. Dec. 1967.

*Primary Examiner*—Stewart J. Levy
*Assistant Examiner*—Joseph W. Joskos
*Attorney, Agent, or Firm*—Gary A. Samuels

[57] ABSTRACT

A method is described for determining the degree of moisture vapor transmission of certain materials which comprises taking a weighed test cup containing a saturated salt solution sealed inside the cup with a waterproof, moisture vapor permeable membrane, and inserting it over a sample that is supported on a waterproof, moisture vapor permeable membrane over a controlled temperature waterbath. After a set time, the cup is reweighed and the water pick up recorded.

2 Claims, 1 Drawing Sheet

TEST METHOD FOR DETERMINATION OF MOISTURE VAPOR TRANSMISSION RATE

FIELD OF THE INVENTION

The test method of the invention provides a way to easily screen water vapor permeable materials for moisture vapor transmission rate (MVTR). The test method of the invention allows for accurate and reproducible MVTR values for materials, such as some textiles, that pass moisture vapor at a high rate. At high rates it is difficult for some tests to differentiate between rates. By utilizing the method of the invention, such materials can be evaluated and compared by the moisture vapor transmission values obtained by the method of this invention.

BACKGROUND

It is useful to have a test method for the determination of moisture vapor transmission rate (MVTR) of highly permeable materials. Hereafter, these materials will be discussed by reference to clothing textiles, but it is understood that the test of the invention is not limited to clothing textiles. Wear trials with clothing have shown a positive correlation of perceived comfort and thermophysiological heat regulation with textile moisture vapor permeability. The human body produces sweat, which by evaporation carries away heat and cools the body. The evaporation of the sweat and dissipation of the vapor is necessary for regulation of body temperature. (See Hollies et al, "Clothing Comfort" Ann Arbor Scientific, published in 1977). Under conditions of heat stress, the rate of sweat production can reach 18,000 g/[m$^2$×24 hrs.]. (See Kerslake, "The Stress of Hot Environments" University Press, Cambridge 1972). An MVTR test method for textiles should have the ability to measure transmission rates at least equal to the rate of possible sweat production. Also, the test method MVTR values should be in approximate proportion to the actual moisture vapor permeance of the textiles.

It has also been shown that various natural and synthetic polymers may exhibit different permeabilities, depending on the humidity of their surroundings (Diffusion in Polymers, Eds. Crank, J. and Park, G. S. Academic Press, London and New York, 1968). Measurement under one condition may not be indicative of performance in a different condition. Humidity within garments can achieve high levels during heat stress; the most stressful situations have high external humidity also. An MVTR test for clothing textiles should simulate these conditions of high physiological demand for MVTR.

A number of test methods are known for the determination of moisture vapor transmission through materials. In one type test, the upright water cup method, a sample is cut to fit snugly in the mouth of a test cup that is partially filled with water. Air of known relative humidity is moved across the cup, drawing moisture vapor through the sample. The test is isothermal. The ASTM Method E96-80-B and the SATRA Permeability/Absorption Test are examples of this type test.

Limitations of the upright cup test methods are listed below:

(1) It is critical that the temperature and the relative humidity of the room, as well as the wind velocity be closely controlled, making the test expensive to operate.

(2) The head space between the sample and the water inside the cup must be standardized, typically at ¾-1 inch. Too small a head space makes cup handling difficult as any water accidentally splashed onto the sample may alter the MVTR value. However, as the head space increases, MVTR values decline, necessitating a long test time. A 24 hour test time is typical. Also, as the head space increases, the test loses ability to discriminate among moderate and high permeabilty materials, and MVTR loses proportionality to permeance.

(3) High permeance materials cause the humidity of the sample under surface to deviate from the nominal relative humidity of 100%, and to approach the relative humidity of the test room.

Saryan, Sarkin S., in an article, "A Method of Determination of Water Vapor Absorption and Simultaneous Transmission through Shoe Upper Materials", presented at the annual meeting of AlCA in June, 1968, describes an upright water cup method. He utilizes gauze in the cup to mitigate water splashing onto the leather samples. However, other limitations of the upright cup method as outlined above are still present.

Seligsberger, Ludwig, in an article "A Versatile Method for Measuring the Water Vapor Absorption of Leather and Other Sheet Materials", presented at the XIth conference of the IULCS on Sept. 9, 1969, describes an upright water cup method which eliminates the head space completely by placing wicking felt into the cup of water, placing a microporous vapor-permeable, waterproof membrane upon the felt and placing the sample upon the membrane. However, the method is not isothermal and calls for a warmer temperature in the cup than in the air, adding an additional limitation to the test. Other upright water cup test limitations yet remain.

Another known type test is inverted cup testing. The testing is similar to the upright cup method except that the measuring cup is inverted, placing the sample in direct water contact. The ASTM Method E96-80 also describes this type of test.

Limitations of this test are listed below:

(1) Again the temperature, relative humidity, and wind velocity must be closely controlled.

(2) materials to be tested must be waterproof.

(3) MVTR is limited by the permeance of the boundary air layer which is influenced by cup face design, and air turbulence, as well as wind velocity.

Another known method for moisture vapor transmission determination is called the modified desiccant method. This is currently used with low-absorbing materials such as fabrics. In this method, a porous, non-hydrophilic, waterproof, vapor-permeable membrane is supported by a floating hoop large enough to hold the sample and test cup assembly described below. The hoop with the membrane is floated upon a temperature controlled water bath. The sample sits upon the membrane. A desiccant cup is made by partially filling a cup with a solution of saturated potassium acetate salt, with excess salt. The mouth of the cup is sealed with similar membrane used in the hoop. The desiccant salt cup is weighed and placed upon the sample for a predetermined time, reweighed, and the MVTR is calculated from the water weight pickup. This method eliminates many of the limitations of the upright cup type test. Specifically, there is no need for tight humidity control in the room as there is no air-sample interface. The problems associated with a head space of air between the sample and the water are eliminated with the use of the vapor-permeable waterproof membrane. However, the method still has limitations of practicality and performance simulation. Potassium acetate has an equilibrium relative humidity of about 20%. This low humidity causes the salt to absorb moisture vapor from typical laboratory air. Spilled crystals will form a slimy film which spreads and is difficult to completely remove from laboratory surfaces. Desiccant cups exposed to air will absorb moisutre, reducing their useful life. Also, the upper side of the test material is exposed to a low relative humidity, atypical of many applications. Solubility of potassium acetate is about 230 gm/100 gm water. This high solubility causes a large quantity of salt to enter solution when moisture transfers into the cup, and useful cup life, until all excess salt has entered solution, is therefore short. To achieve a practical useful life, the solution must be mixed with an initial salt concentration that results in a paste-like consistency that makes intimate contact between the desiccant and the cup membrane difficult to achieve. Furthermore, desiccant preparation requires more than 12 hours to achieve uniform mixing of the saturated solution with the excess salt.

The present invention provides a more satisfactory test method of measuring MVTR by using a different salt, especially in determining Moisture Vapor Transmission Rate (MVTR) of highly permeable materials such as textiles. Different materials have been tested by this method and it has been determined that they can be evaluated and compared for permeability by the MVTR values obtained by this test. The test gives reproducible results that are not easily influenced by operator error.

SUMMARY OF THE INVENTION

Figure 1:
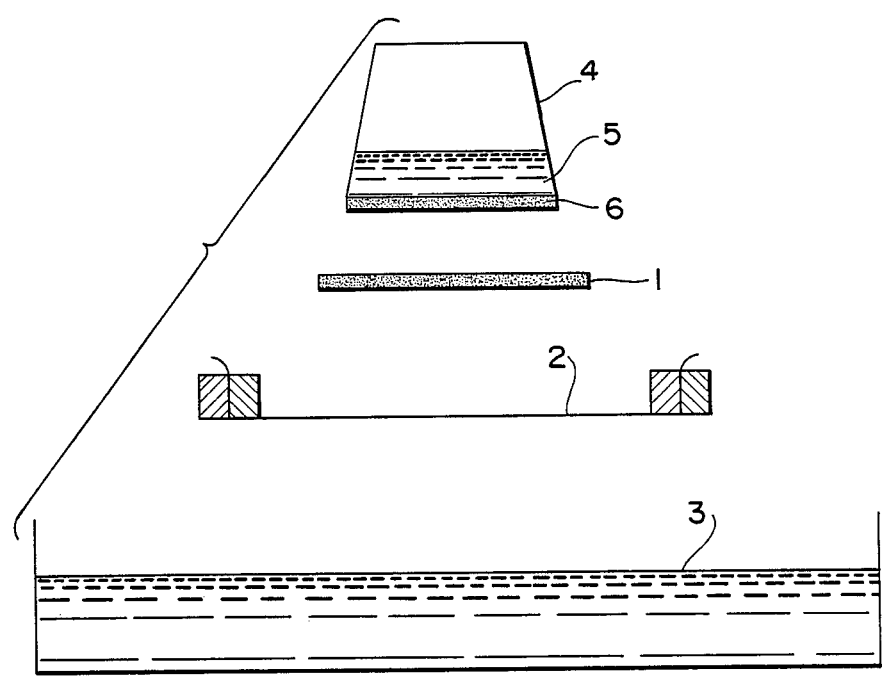
FIG. 1 is an expanded view of the test assembly of the invention.
Figure 2:
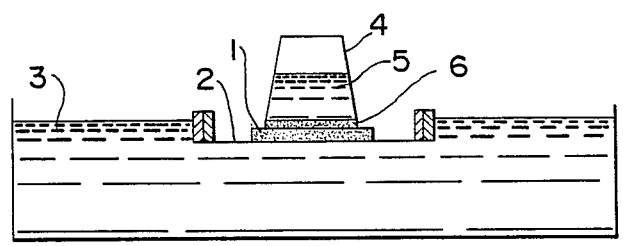
FIG. 2 is a view of the test assembly of the invention.

Referring to FIGS. 1 and 2, the test method of this invention comprises, in combination with the proper salt selection, the following sequence:

(i) placing the sample to be tested onto a waterproof, moisture vapor permeable membrane (1) in a support (2) on a controlled temperature water bath (3) held at a temperature that is substantially the same as the test environment, (ii) inverting a weighed test cup (4), which contains a saturated salt solution (5) and is sealed with a waterproof, moisture vapor permeable membrane (6), onto the sample.

(iii) after a predetermined time, weighing the cup and recording the water pickup over the weight of the cup prior to step ii.

To translate the weight pickup into a means for comparing transmission rates between materials, MVTR is calculated according to the following formulation:

$$MVTR\ (g/[m^2 \times \text{time of test}]) = \frac{\text{(Weight (g) water pickup in cup)}}{\text{[Area } (m^2) \text{ of cup mouth}} \times \text{Time of test])}$$

The salt used is described further below.

DETAILED DESCRIPTION OF THE INVENTION

Preferred membranes are microporous, moisture vapor permeable membranes of expanded poly(tetrafluoroethylene), (ePTFE), such as are described in U.S. Pat. No. 3,953,566. Other types of membranes that can be used include those made from breathable polyurethanes. It is sufficient that the two membranes used in the test method of this invention be moisture vapor permeable. However, preferably, the combined moisture vapor permeability of the two membranes should be high enough to yield an MVTR of at least about ten times that of the sample.

A preferred salt is sodium chloride. Saturated salt solutions of certain salts maintain definite relative humidities at constant temperature. These solutions should have a surplus of the salts to ensure saturation at all times. Other useful salts include potassium chloride. It is sufficient that the salt have: (1) an equilibrium relative humidity which simulates appropriately end use conditions and which is greater than the humidity of the room in which the test method is conducted. Preferably this relative humidity is greater than 20%, more preferably more than 50%, and most preferably greater than 70%, (2) solubility low enough that the desiccant cups have a practical useful life, and (3) the solution be free flowing with excess salt present. Sodium chloride as a preferred salt fulfills these criteria, maintaining an equilibrium relative humidity of about 76%, a solubility of 35 g/100 gm water, and free flow.

The preferred temperature of the test is 23° C. Increasing temperature will increase measured MVTR, and decreasing temperature will decrease measured MVTR. Any temperature can be used at which the salt will form a practical desiccant of known relative humidity.

Experiments were conducted to demonstrate the ability of the test method to measure high transmission rates, and rates approximately proportional to the material permeability.

To demonstrate the high transmission rates obtainable with this invention, the test was conducted with no sample between the two ePTFE membranes of the hoop and the cup. Temperature was 23° C. and sodium chloride was the desiccant salt. The measured average MVTR was about 34,200 g/[m² × 24 hr.] One layer of the same membrane was tested by ASTM E96-80-B at 23° C. and 50% relative humidity. The measured average MVTR was about 1120 g/[m² × 24 hr.].

To demonstrate approximate proportionality to permeability, a material comprised of ePTFE laminated to a nylon taffeta was tested in a single layer, then two layers, and four layers. Each additional layer reduces the total permeability proportionately. Tests were conducted by ASTM E96-80-B (23° C., 50% RH) and by the method of the invention (at 23° C.) using sodium chloride as the desiccant salt. Results are shown in Table 1.

TABLE 1

EFFECT OF ADDITIONAL LAYERS OF IDENTICAL MATERIALS ON MVTR.

| | MVTR (g/[m² × 24 hr.]) | |
|---|---|---|
| Number of Layers of Test Material | Method of the Invention | ASTM-E96-80-B |
| 4 | 1130 | 820 |
| 2 | 2620 | 950 |

TABLE 1-continued

EFFECT OF ADDITIONAL LAYERS OF IDENTICAL MATERIALS ON MVTR.

| Number of Layers of Test Material | MVTR (g/[m² × 24 hr.]) | |
|---|---|---|
| | Method of the Invention | ASTM-E96-80-B |
| 1 | 4880 | 1020 |

Clearly, proportionality is much more nearly approached by the method of the invention.

Variations of the method are also possible. For example, the sample material can be clamped into the hoop in place of the membrane which is commonly placed in the hoop. In this case, the sample material must itself be waterproof. In this variation, the upper limit of measurable MVTR can reach about 70,000 g/[m²×24 hr]. In another variation, the sample material can be sealed directly to the open cup face, in place of the membrane which is commonly sealed to the cup. The sample material must be waterproof.

What is claimed is:

1. A method for determining the degree of moisture vapor transmission of certain materials that transmit water in amounts that affect moisture vapor transmission values, which comprises, in sequence:
   (i) placing a sample of the material onto a waterproof, moisture vapor permeable membrane in a support on a controlled temperature water bath held at a temperature that is substantially the same as the test environment,
   (ii) inverting a weighed test cup which contains a saturated salt solution and is sealed with a waterproof, moisture vapor permeable membrane onto the sample, said salt having an equilibrium relative humidity higher than that of the atmosphere in which the method is carried out, and in which a solution of the salt is free flowing at ambient conditions,
   (iii) after a predetermined time, weighing the cup and recording the water pickup over the weight of the cup prior to step ii,
   (iv) determining the moisture vapor transmission rate.

2. The method of claim 1 where the material is clothing textiles.

* * * * *